United States Patent [19]

Schock et al.

[11] Patent Number: 5,540,653
[45] Date of Patent: Jul. 30, 1996

[54] PREASSEMBLED BYPASS CIRCUIT

[75] Inventors: Robert B. Schock, Sparta; Robert L. Wilcox, Wanaque, both of N.J.

[73] Assignee: Datascope Investment Corp., Montvale, N.J.

[21] Appl. No.: 965,438

[22] Filed: Oct. 23, 1992

[51] Int. Cl.$^6$ .................................................. A61M 1/03
[52] U.S. Cl. ........................................................ 604/7
[58] Field of Search ............................ 604/122, 4, 7, 604/80, 81, 250, 262, 261

[56] References Cited

U.S. PATENT DOCUMENTS

| | | | |
|---|---|---|---|
| 2,800,904 | 7/1957 | Bellato | 128/214 |
| 3,881,483 | 5/1975 | Sausse | 604/4 |
| 3,890,969 | 6/1975 | Fischel | 604/4 |
| 3,949,734 | 4/1976 | Edwards et al. | 604/4 |
| 4,299,705 | 11/1981 | Russell | 210/647 |
| 4,540,399 | 9/1985 | Litzie et al. | 604/122 |
| 4,610,656 | 9/1986 | Mortensen | 604/4 |
| 4,642,098 | 2/1987 | Lundquist | 604/123 |
| 4,770,787 | 9/1988 | Heath et al. | 210/646 |
| 5,004,548 | 4/1991 | Richalley et al. | 210/646 |
| 5,041,215 | 8/1991 | Chamberlain, Jr. et al. | 210/136 |
| 5,171,212 | 12/1992 | Buck et al. | 604/4 |

OTHER PUBLICATIONS

The Bard CPS React System (Marketing Brochure) (1990).

*Primary Examiner*—C. Fred Rosenbaum
*Assistant Examiner*—Manuel Mendez
*Attorney, Agent, or Firm*—Fitzpatrick, Cella, Harper & Scinto

[57] ABSTRACT

A preassembled PBY circuit includes a blood pump, an oxygenator, a blood line, a filter/trap, a cannulae line subassembly, and a return line. The blood pump, oxygenator, blood line, filter/trap, cannulae line subassembly, and return line are serially arranged in a closed loop configuration, and a prime line is attached in fluid communication with the circuit. The cannulae line subassembly includes a first cannula line attached to the return line, a second cannula line attached to the filter/trap, and a removable connector for connecting the first and second cannulae lines in fluid communication. Each of the cannulae lines is prearranged in a helical configuration. The circuit is arranged for suspension, such that, when suspended, the filter/trap is located at a high point of the circuit, and the prime line is attached at a low point of the circuit. In this manner, priming fluid is introduced through the prime line, enters at a low point of the circuit, and fills the circuit in a bottom-to-top priming operation.

45 Claims, 3 Drawing Sheets

PREASSEMBLED BYPASS CIRCUIT

BACKGROUND OF THE INVENTION

1. Field of the Invention

The present invention relates generally to medical devices and procedures. More particularly, it relates to a preassembled circuit for use in extracorporeal procedures, such as coronary bypass and univentricular bypass procedures.

2. Description of the Prior Art

Extracorporeal procedures, such as coronary bypass and univentricular bypass procedures, are well known. Generally, in these procedures it is necessary to provide an extracorporeal fluid path to bypass all or a portion of an artery, vein or organ, such as the heart or lungs, to maintain a proper blood flow. Such an extracorporeal fluid path may be required to allow surgery on the affected artery, vein, organ, or portion thereof. Moreover, where an extracorporeal bypass circuit provides an artificial fluid path for an affected organ, it also may be necessary to provide apparatus for supporting an organ function. For example, during coronary bypass procedures, an extracorporeal circuit may provide a blood pump and oxygenator for supporting the heart and lung functions. Thus, an extracorporeal procedure generally includes a first cannula inserted in a vessel upstream of the affected site, a second cannula inserted in the vessel downstream of the affected site, and a series of tubes and, if required, additional support apparatus such as a pump and the like, attached in fluid communication between the two cannulae.

Recently, a percutaneous bypass (PBY) procedure has been utilized in clinical studies for treatment of cardiac arrest patients. However, a recent survey of such PBY procedures in 51 cardiac arrest patients demonstrates the criticality of rapid initiation of the PBY procedure. Of the 51 patients surveyed, 19 had flow established within 15 minutes of cardiac arrest, while 32 patients did not have flow established within 15 minutes of cardiac arrest. Of the 19 patients which received PBY within 15 minutes, all survived initially, and 13 of the 19 were discharged from the hospital. Of the 32 patients which did not receive PBY within 15 minutes of cardiac arrest, none survived. Thus, a critical aspect of successful PBY procedure is rapid initiation.

A drawback of known bypass circuits and procedures is the time required for setting up the circuit preparatory to performing the procedure. Specifically, any support apparatus first must be located, sterilized, assembled and attached to appropriate sterilized circuit tubing. Then, the entire circuit must be primed with a biocompatible fluid, such as blood or saline, to completely flush out any air pockets in the circuit. If present, such air pockets could result in an air embolism passing through the circuit into the patient, which could cause death or serious injury to the patient.

Preassembled PBY circuits are known. For example, one known system includes a femoral access cannulae kit, a hardware assembly and a preassembled and sterilized circuit of tubes for connecting the femoral cannulae and the various hardware. The hardware generally is assembled on a cart, and includes a blood pump, a membrane oxygenator, a gas supply, and a heat exchanger. However, when this system is set up and primed, fluid is required to flow up and down through various segments of the circuit, which traps air at certain high points in the circuit. Thus, safe assembly of the system circuit includes 74 steps, 30 of which are directed to priming procedures that include manipulating and tapping tubing to eliminate air traps and bubbles. Although a few clinicians have found success with this system by training a highly skilled team for rapid set-up, the large number of steps required for set-up and priming, and the criticality of response time required for successful procedure, have intimidated users and discouraged widespread use of a PBY system and procedure in cardiac arrest patients. Accordingly, a need exists for an improved preassembled bypass circuit having a rapid priming configuration.

SUMMARY OF THE INVENTION

The present invention provides an improved preassembled circuit for extracorporeal procedures such as PBY, full heart, or univentricular bypass procedures, for rapid set-up and priming preparatory to procedure. It overcomes drawbacks of the prior art by providing a combination of preassembled circuit components arranged for bottom-to-top priming.

In one aspect, the present invention is a preassembled PBY circuit, including a blood pump, an oxygenator, a blood line, a filter/trap, a cannulae line subassembly, and a return line. The blood pump, oxygenator, blood line, filter/trap, cannulae line subassembly, and return line are serially arranged in a closed loop configuration, and a prime line is attached in fluid communication with the circuit. The cannulae line subassembly includes a first cannula line attached to the return line, a second cannula line attached to the filter/trap, and means for connecting the first and second cannulae lines in fluid communication. The circuit is arranged for suspension such that, when suspended, the filter/trap is located at a high point of the circuit, and the prime line is attached at a low point of the circuit. In this manner, priming fluid introduced through the prime line enters the return line at a low point of the circuit, and fills the circuit in a bottom-to-top priming operation.

In another aspect, each of the cannulae lines is prearranged in a helical configuration, and the cannulae line subassembly is prepackaged in a sterile tear-apart bag, two-piece breakaway housing, or the like, to maintain the cannulae lines in a configuration having a continuous vertical rise, such as a helical configuration, when the circuit is suspended. After priming, the prepackaging readily is removed, and the sterile cannulae lines are disconnected at the connecting means and attached to respective arterial and venous cannulae for performing a bypass procedure.

In another aspect, the present invention is a preassembled circuit for a univentricular or full heart bypass procedure without oxygenation. In this embodiment, the circuit includes a blood pump, a blood line, a filter/trap, a cannulae line subassembly, and a return line. The blood pump, blood line, filter/trap, cannulae line subassembly and return line are serially arranged in a closed loop configuration, and a prime line is attached in fluid communication with the circuit. The cannulae line subassembly includes a first cannula line attached to the return line, a second cannula line attached to the filter/trap, and means for connecting the first and second cannulae lines in fluid communication. The circuit is arranged for suspension such that, when suspended, the filter/trap is located at a high point of the circuit, and the prime line is attached at a low point of the circuit. In this manner, priming fluid is introduced through the prime line, enters at a low point of the circuit, and fills the circuit in a bottom-to-top priming operation.

In another aspect, the present invention is a preassembled circuit for an extracorporeal procedure, including a blood pump, an oxygenator, a blood line, a filter/trap, a cannulae line subassembly, and a heat exchanger line subassembly. The blood pump, oxygenator, blood line, filter/trap, cannulae line subassembly and heat exchanger line subassembly are serially arranged in a closed loop configuration, and a prime line is attached in fluid communication with the circuit. The cannulae line subassembly includes a first cannula line attached to the heat exchanger line subassembly, a second cannula line attached to the filter/trap, and means for connecting the first and second cannulae lines in fluid communication. The heat exchanger line subassembly includes a heat exchanger reservoir line and a reservoir bypass line. The reservoir line is connected at one end to a first end of the reservoir bypass line proximate the cannulae line subassembly, and is connected at its other end to a second end of the reservoir bypass line proximate the blood pump. The circuit is arranged for suspension such that, when suspended, the filter/trap is located at a high point of the circuit, and the prime line is attached at a low point of the circuit. In this manner, priming fluid introduced through the prime line enters at a low point of the circuit, and fills the circuit in a bottom-to-top priming operation.

In another aspect, the present invention is a preassembled circuit for an extracorporeal bypass procedure including a pump line or tube, a blood line, a filter/trap, a cannulae line assembly, and a return line. The pump line, blood line, filter/trap, cannulae line assembly and return line are serially arranged in a closed loop configuration, and a prime line is attached in fluid communication with the circuit. The cannulae line subassembly includes a first cannula line attached to the return line, a second cannula line attached to the filter trap, and means for connecting the first and second cannulae lines in fluid communication. The circuit is arranged for suspension such that, when suspended, the filter/trap is located at a high point of the circuit, and the prime line is attached at a low point of the circuit. In this manner, priming fluid is introduced through the prime line, enters at a low point of the circuit, and fills the circuit in a bottom-to-top priming operation.

These and other aspects, features and advantages of the present invention readily will be apparent to those skilled in the art from the following detailed description of the present invention and the accompanying drawings.

DETAILED DESCRIPTION OF THE PREFERRED EMBODIMENTS

Figure 2:
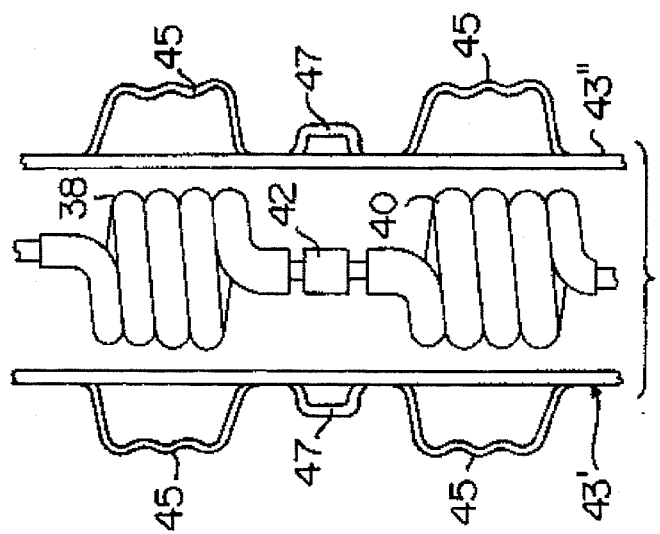
FIG. 2 is an exploded side view of one embodiment of a cannulae line subassembly of the present invention, illustrating a two piece break-apart housing for securely holding the first and second cannulae lines and connector in a compact continuous direction configuration such that, when suspended, each cannula line is helically wound to provide a continuous vertical rise in the fluid path for bottom-to-top priming.
Figure 1:
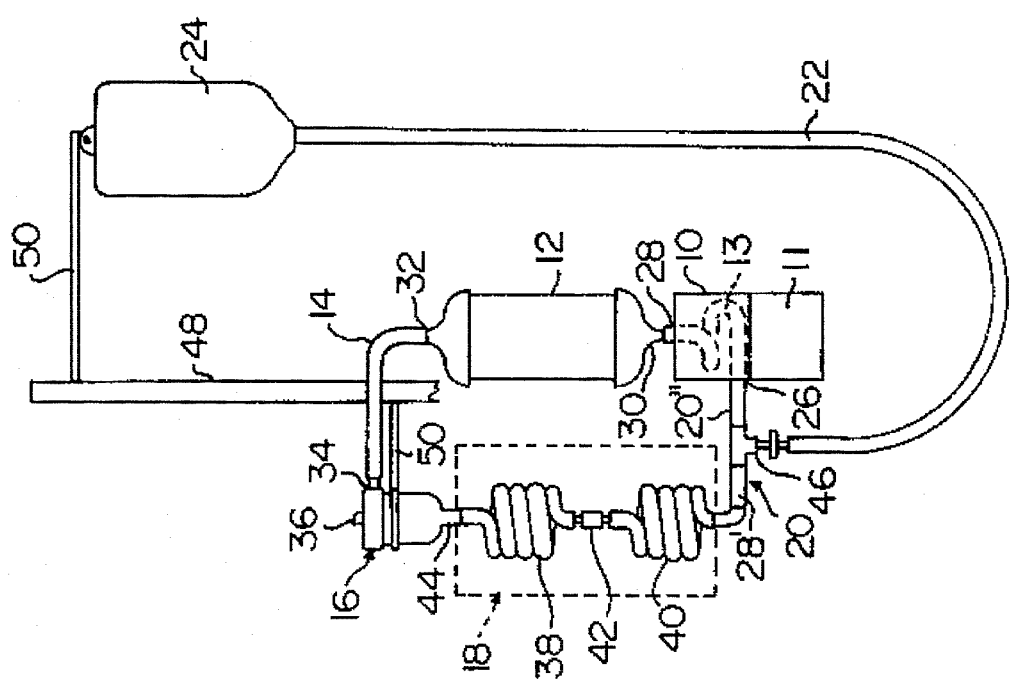
FIG. 1 is a plan view of a preassembly PBY circuit of the present invention, illustrating a blood pump, an oxygenator, a blood line, a filter/trap, a cannulae line subassembly and a return line arranged in a suspended closed-loop configuration for rapid bottom-to-top priming by a prime line and priming fluid source.

Referring now to the drawings, wherein like reference numerals designate like or similar parts throughout, FIGS. 1 and 2 illustrate an embodiment of a preassembled PBY circuit according to the present invention.

The preassembled PBY circuit generally includes a blood pump 10, an oxygenator 12, a blood line 14, a filter/trap 16, a cannulae line subassembly 18 and a return line 20 arranged in a closed-loop configuration to provide a continuous flow path therethrough. A prime line 22 and priming fluid source 24 are connected to return line 20, in fluid communication therewith.

Blood pump 10 may be any conventional pump, and preferably provides a continuous blood flow chamber. In the embodiment of FIG. 1, blood pump 10 is a roller pump, which includes a continuous blood flow chamber formed by a flexible tube 13 (shown in phantom), and is driven by a conventional motor 11. For example, blood pump 10 may be a single roller blood pump as disclosed in copending U.S. patent application Ser. No. 07/898,673. In that pump, a flexible tube generally is wound in a helical turn from an inlet port 26, located at a side portion of pump 10, to an outlet port 28, located at an end of pump 10, as shown in phantom in FIG. 1. As will be discussed in greater detail below, this arrangement provides for safe rapid priming of pump 10.

Oxygenator 12 may be any conventional oxygenator suitable for PBY procedure. One such suitable oxygenator is a SAFE-1 membrane oxygenator manufactured by Polystan A/S. Inlet 30 of oxygenator 12 is connected in fluid communication with outlet port 28 of blood pump 10 by conventional means, such as a tube or the like. Alternatively, blood pump 10 and oxygenator 12 may be arranged as a single unit, as disclosed in copending U.S. Pat. application Ser. No. 07/898,673. In each case, oxygenator 12 is arranged for in-line flow to facilitate safe rapid priming, as described in greater detail below.

Oxygenator 12 is connected in fluid communication with filter/trap 16 by blood line 14. More specifically, one end of blood line 14 is connected to outlet 32 of oxygenator 12, and the other end of blood line 14 is connected to an inlet 34 of filter/trap 16. Blood line 14 is a standard tube having a diameter sufficient for PBY procedures. In the present embodiment, blood line 14 is a ⅜ inch inner diameter tube made of polyvinylchloride (PVC). Of course, those skilled in the art readily will be able to select alternative tubing suitable for PBY procedures.

Filter/trap 16 also may be any conventional filter/trap suitable for PBY procedure. As shown in FIG. 1, filter/trap 16 is an arterial filter that includes a bleed valve 36, which provides means for venting any air trapped in filter/trap 16 to ambient air. Bleed valve 36 preferably includes an air permeable/fluid impermeable barrier such that only air may vent out of filter/trap 16. One such suitable filter/trap is an AutoVent SP, manufactured by Pall Biomedical Products Corporation. However, those skilled in the art readily will be able to select alternative filter/traps and means for venting air disposed in the circuit to ambient, as described in greater detail below.

Cannulae line subassembly 18 includes an arterial line 38, a venous line 40 and a connector 42. Each of cannulae lines 38, 40 is a standard flexible tube suitable for PBY cannulation, as is well known in the art. In the present embodiment, each of cannulae lines 38, 40 is a ⅜ inch inner diameter tube composed of PVC. Arterial line 38 is connected at one end to an outlet 44 of filter/trap 16, and at the other end to one end of venous line 40 by a conventional connector 42, such as a two-headed, barbed fitting. The other end of venous line 40 is attached to return line 20, in fluid communication therewith.

Referring now to FIG. 2, one embodiment of a cannulae line assembly of the present invention is illustrated in an exploded view. In this embodiment, the cannulae line subassembly includes arterial cannula line 38, venous cannula line 40, connector 42, and housing portions 43', 43". As shown therein, housing portions 43', 43" are preformed with respective helical guide compartments 45 and connector compartments 47 for receiving the helically coiled cannulae lines 38, 40 and connector 42, and for securely holding them in a configuration that maintains a continuous vertical rise when the assembly is suspended for priming (see, e.g., FIG. 1). Housing portions 43', 43" are provided with a conventional interlocking peripheral structure so that they may be snapped together and pulled apart, as is well known in the art. Housing portions 43', 43" may be composed of conventional materials, such as a clear, lightweight plastic, and may be formed by conventional methods, such as press or blow molding. Of course, those skilled in the art readily will recognize alternative means and structure for securely holding cannulae lines 38, 40 in respective helical coils having a continuous vertical rise for bottom-to-top priming.

Referring again to FIG. 1, return line 20 includes a 3-way connector valve 46 and return line portions 20', 20". Return line portions 20', 20" may be any standard tubing suitable for PBY procedure, and in the present embodiment are ⅜ inch inner diameter tubes made of PVC. The 3-way connector valve 46 also is a conventional valve, such as a Y-connector or a T-connector valve, and return line portions 20', 20" are connected to the two open ends of the 3-way connector valve 46.

Prime line 22 is connected at one end to the valve end of 3-way connector valve 46, and at the other end to priming fluid source 24. As is well known in the art, priming fluid source 24 may be a sterile bag that contains a volume of priming fluid, such as blood, saline solution or the like, for priming the preassembled circuit by gravity feed. Alternatively, priming fluid source 24 may be a secondary pump that is connected to a priming fluid reservoir. Of course, in such case the priming fluid source would not have to be suspended for gravity feed. Those skilled in the art readily will appreciate alternative equivalent structures for priming fluid source 24.

Preparatory to PBY procedures the PBY circuit is primed using a bottom-to-top priming operation. Specifically, the PBY circuit first is attached to a pole 48, such as a hospital crash cart pole, by conventional support structure 50, such that the circuit is suspended in a vertical configuration for priming. Of course, the circuit alternatively could be packaged pre-attached to a standard crash cart pole, to maintain the components in positions optimal for priming. When suspended, as shown in FIG. 1, the circuit components provide a split path from return line 20, located at the low point of the circuit, to filter/trap 16, located at the high point of the circuit. Specifically, one path includes return line 20', cannulae line assembly 18, and filter/trap 16. The other path includes return line 20", blood pump 10, oxygenator 12, blood line 14 and filter/trap 16. Each of these paths provides a continuous vertical flow path between the low point and the high point. Moreover, the flow path in each component of the system has a continuous vertical rise. In particular, the pump chamber (tube 13) of pump 10, and each of the cannulae lines 38, 40 are arranged in a helical coil having a continuous vertical rise. Accordingly, during priming, fluid flows from bottom-to-top only, thereby substantially eliminating any risk of bubble entrapment in the circuit during priming.

For example, as shown in FIG. 1, priming fluid source 24 may be suspended from pole 48 at a height above filter/trap 16 (the high point of the circuit) and, if not preassembled, prime line 22 may be connected between priming fluid source 24 and 3-way connector valve 46 of return line 20. The 3-way connector valve 46 then is opened to permit gravity flow of the priming fluid from priming fluid source 24 through prime line 22 into the PBY circuit. As priming fluid flows into the PBY circuit it will fill the circuit from return line 20 (the low point) to filter/trap 16 (the high point) by displacing air disposed in the circuit. The displaced air is vented to ambient air through bleed valve 36, until the PBY circuit is fully primed. In other words, the PBY circuit is primed bottom-to-top by gravity feed. After the PBY circuit is fully primed, prime line 22 may be closed or disconnected at 3-way valve 46, and pump 10 may be activated to circulate the prime fluid through the PBY circuit. In this manner, any air bubbles that may have formed during the bottom-to-top priming procedure will be circulated to filter/trap 16, captured therein, and vented to ambient. After appropriate recirculation, arterial cannula line 38 and venous cannula line 40 are clamped, disconnected from cannulae line connector 42, and connected to respective arterial and venous cannulae (not shown) for PBY procedure. Finally, oxygen ($O_2$) flow to oxygenator 12 may be initiated, and the cannulae may be inserted in the patient to commence PBY procedure.

Figure 3:
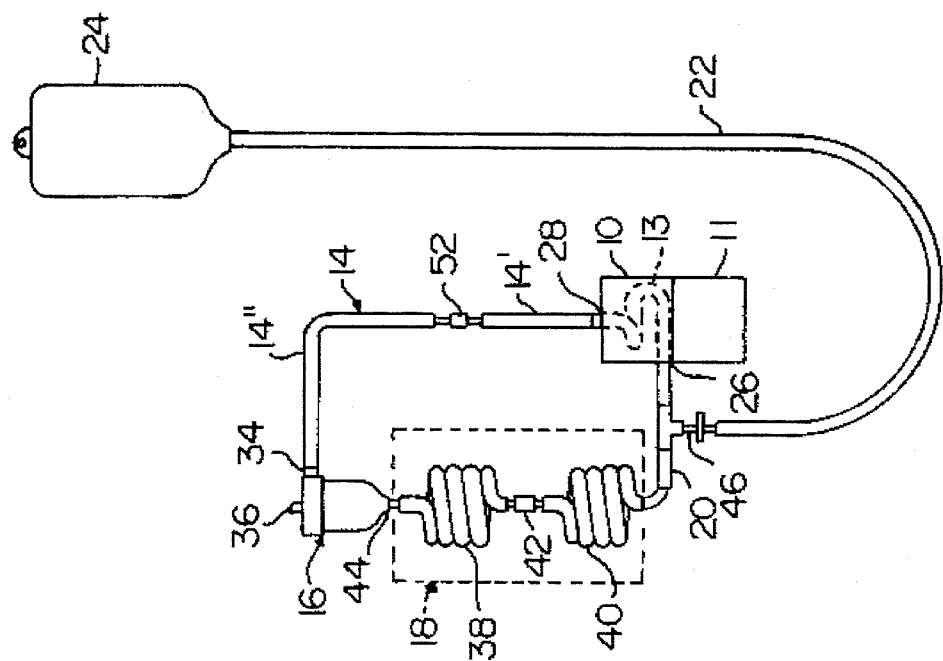
FIG. 3 is a plan view of a preassembled full heart or univentricular bypass circuit of the present invention, illustrating a blood pump, a blood line, a filter/trap, a cannulae line subassembly and a return line arranged in a suspended closed-loop configuration for rapid bottom-to-top priming by a prime line and priming fluid source.

FIG. 3 illustrates in plan view a second embodiment of a preassembled circuit according to the present invention. The constitution, arrangement and priming operation of this embodiment is substantially similar to that of the first embodiment, except that no oxygenator is provided in the preassembled circuit. This embodiment has particular utility in a univentricular bypass procedures or a full heart bypass procedure without the use of an oxygenator.

Of course, the circuit of the second embodiment readily may be adapted to include an oxygenator. Specifically, in this embodiment, blood line 14 includes first and second blood line portions 14', 14" and a connector 52. For example, connector 52 may be a two-headed barbed fitting. Thus, it will be appreciated that either preparatory to, or after initiation of, a procedure such as a full heart bypass procedure, connector 52 may be removed and an oxygenator 12 may be inserted therefore.

Figure 4:
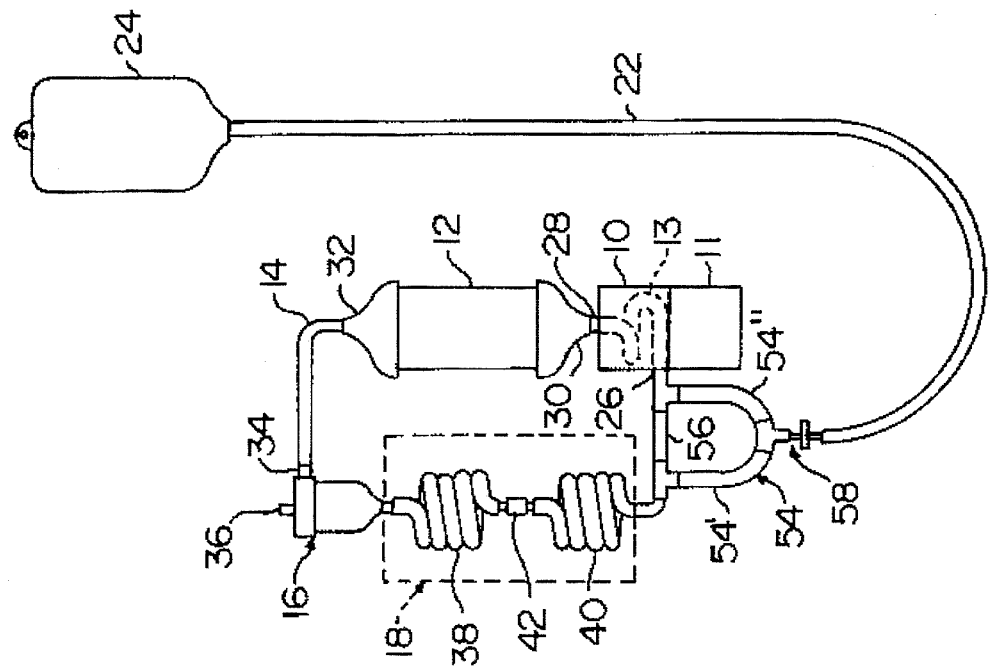
FIG. 4 is a plan view of another preassembled PBY circuit of the present invention, illustrating a blood pump, an oxygenator, a blood line, a filter/trap, a cannulae line subassembly, and a heat exchanger line subassembly arranged in a suspended closed-loop configuration for rapid bottom-to-top priming by a prime line and priming fluid source.

FIG. 4 illustrates a third embodiment of the present invention which also has particular utility in PBY procedures. In this embodiment, the constitution, arrangement and operation of the circuit also is substantially similar to that of the first embodiment. However, in the embodiment of FIG. 4, return line 20 is replaced by a heat exchanger line subassembly. The heat exchanger line subassembly includes a heat exchanger reservoir line 54, and a reservoir bypass line 56. More specifically, reservoir bypass line 56 is a tube which is attached at a first end to venous cannula line 40, and at a second end to inlet port 26 of pump 10. Reservoir line 54 is attached at one end to the first end of reservoir bypass line 56 (proximate venous cannula line 40) and is attached at its other end to the second end of reservoir bypass line 56 (proximate blood pump 10). More particularly, reservoir line 54 includes first and second reservoir line portions 54', 54" and a 3-way connector valve 58. The structure and function of 3-way connector valve 58 is substantially the same as 3-way connector valve 46 of the first embodiment, in that it is located at the low point of the circuit for bottom-to-top priming. In operation, after priming is completed, 3-way connector valve 58 is removed and the free ends of reservoir lines 54', 54" respectively are connected to inlet and outlet ports of a heat exchanger (not shown), as is well known in the art.

Figure 5:
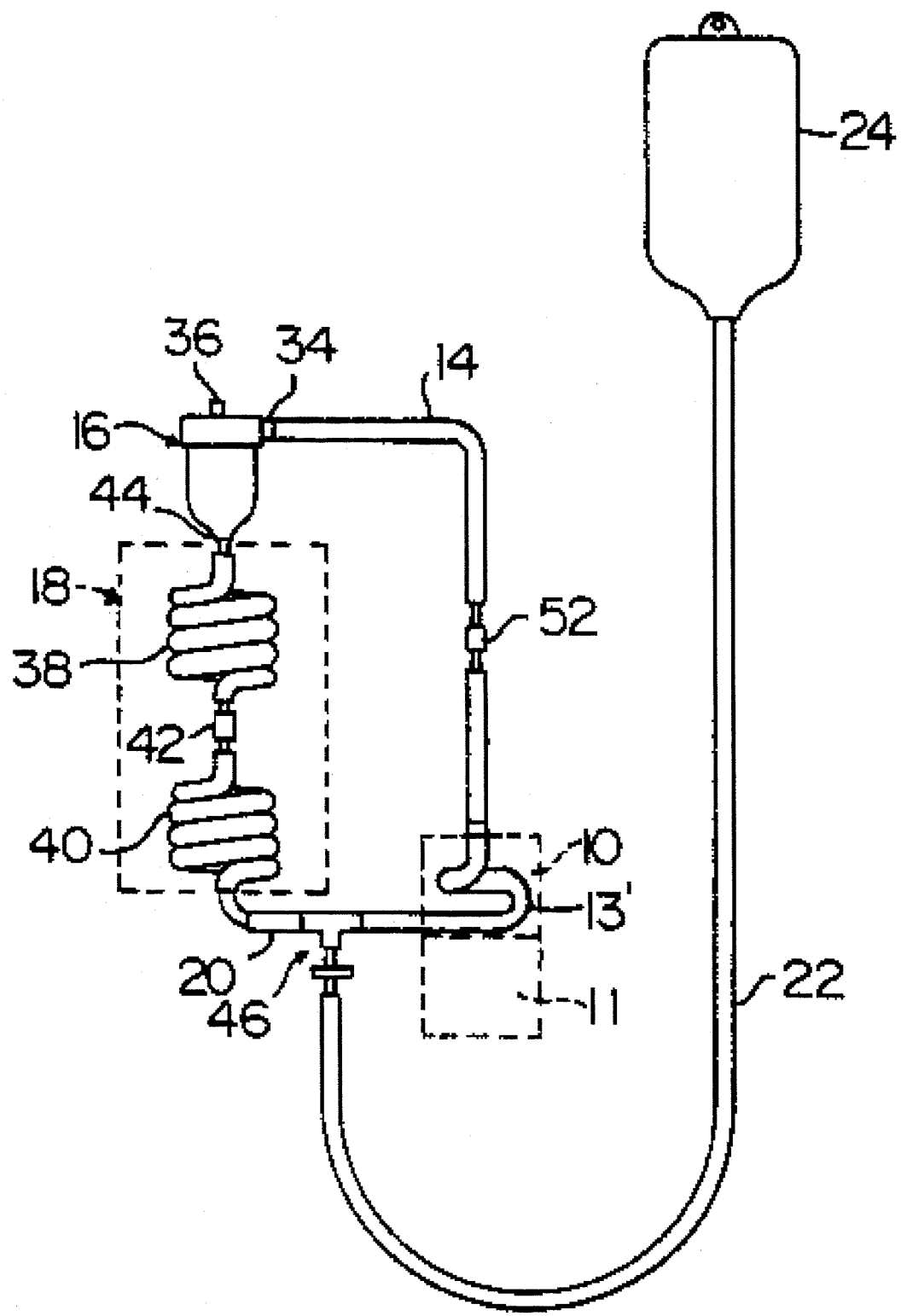
FIG. 5 is a plan view of another preassembled circuit of the present invention, illustrating a pump line, a blood line, a filter/trap, a cannulae line subassembly, and a return line arranged in a suspended closed-loop configuration for rapid bottom-to-top priming by a prime line and priming fluid source.

FIG. 5 illustrates a fourth embodiment of the present invention. In this embodiment, the constitution, arrangement and operation of the circuit is substantially similar to that of the second embodiment. However, in the embodiment of FIG. 5, the pump is replaced with a pump line or tube 13'. The pump line 13' is connected in fluid communication at one end to return line 20, by 3-way valve 46, and at the other end to blood line 14, by connector 52. In the embodiment of FIG. 5, blood line 13'is a ⅜ inch inner diameter PVC tube. Those skilled in the art will appreciate that this circuit readily may be adapted for use in any conventional bypass system which utilizes a pump 10 (shown in phantom) and a standard tube as a pump chamber. Moreover, as in the second embodiment, the circuit of the embodiment of FIG. 5 readily may be adapted to include an oxygenator.

Thus, it will be appreciated that each of these embodiments overcomes drawbacks of conventional extracorporeal circuits by providing a preassembled extracorporeal circuit arranged for bottom-to-top priming. This bottom-to-top priming is facilitated by arranging each circuit path, including each of the various circuit components, to provide a continuous vertical rise when the circuit is suspended for priming. In this manner, air bubbles often trapped in conventional bypass circuits during priming procedures, and the timely procedures required for removing these air bubbles, substantially are eliminated in a simple priming procedure that can be performed by a single clinician. Moreover, fluid loss and risk of contamination due to procedures for attaching various circuit lines and components substantially are eliminated. Finally, since each of the circuit components in these embodiments may be selected from conventional components, such as pre-existing FDA approved components, the preassembled extracorporeal circuit of the present invention is highly cost efficient.

Although the present invention has been described in detail with respect to preferred embodiments thereof, it will be understood that these embodiments are illustrative only, and that the scope of the invention is not limited thereto. Moreover, those skilled in the art readily will appreciate numerous equivalent modifications, variations, or alternative embodiments of the present invention. Accordingly, the scope of the present invention is defined by the following claims, including all equivalents thereto that readily would be apparent to those skilled in the art.

What is claimed is:

1. A prepackaged cannulae line assembly for an extracorporeal circuit, the assembly comprising a first cannula line, a second cannula line, means for connecting the first and second cannula lines, means for connecting at least one of said cannulae lines to priming means, and means for suspending the assembly, the assembly including packaging means for maintaining each of the cannulae lines in a predetermined configuration having a continuous vertical rise when the assembly is suspended for priming.

2. A cannulae line assembly as recited in claim 1, wherein said connector means includes a two-headed, barbed fitting for connecting said first and second cannulae lines.

3. A cannulae line assembly as recited in claim 1, wherein said assembly is prepackaged in container means for maintaining said assembly in a predetermined configuration having a continuous vertical rise when the assembly is suspended for priming.

4. A cannulae line assembly as recited in claim 1, wherein said first and second cannulae lines are prearranged in a helical configuration.

5. A cannulae line assembly as recited in claim 4, wherein said assembly is prepackaged in container means for maintaining said assembly in a helical configuration having a continuous vertical rise when the assembly is suspended for priming.

6. A cannulae line assembly as recited in claim 3, wherein said container means is a break-apart container.

7. A cannulae line assembly as recited in claim 5, wherein said container means is a break-apart container.

8. A preassembled circuit for an extracorporeal bypass procedure, the circuit comprising a pump line, a blood line, a filter/trap, a cannulae line subassembly, and a return line serially arranged in a closed-loop configuration, and means for attaching a prime line in fluid communication with the circuit, the cannula line subassembly including a first cannula line attached to the return line, a second cannula line attached to the filter/trap, and means for connecting the first and second cannulae lines in fluid communication, said circuit being arranged for suspension, such that, when suspended, the filter/trap is located at a high point of the circuit, and the prime line attaching means is located at a low point of the circuit, such that, when a prime line is attached to the circuit line, priming fluid introduced through the prime line enters at a low point of the circuit, and fills the circuit in a bottom-to-top priming operation.

9. A circuit as recited in claim 8, wherein each of said first and second cannulae lines is prearranged in a helical configuration, such that, when the circuit is suspended, said cannulae line subassembly provides a continuous vertical rise for priming.

10. A circuit as recited in claim 8, wherein said cannulae line subassembly is prepackaged in tear-apart container means for maintaining said cannulae lines in a predetermined configuration, such that, when the circuit is suspended for priming, said cannula line subassembly provides a continuous vertical rise for priming.

11. A circuit as recited in claim 9, wherein said cannulae line subassembly is prepackaged in tear-apart container means for maintaining said cannulae lines in a helical configuration, such that, when the circuit is suspended for priming, said cannula line subassembly provides a continuous vertical rise for priming.

12. A circuit as recited in claim 8, wherein said circuit is prepackaged in container means for maintaining each of said pump line, blood line, filter/trap, cannulae line subassembly and return line in a configuration having a continuous vertical rise when said circuit is suspended for priming.

13. A preassembled circuit for an extracorporeal bypass procedure, the circuit comprising a closed-loop circuit configuration including a cannulae line subassembly and means for attaching a prime line in fluid communication with the circuit, the cannulae line subassembly including a first cannula line, a second cannula line, and means for connecting the first and second cannulae lines in fluid communication, said circuit being arranged for suspension, such that, when suspended, the prime line attaching means is located at a low point of the circuit, such that, when a prime line is attached to the prime line attaching means, priming fluid introduced through the prime line enters at a low point of the circuit and fills the circuit in a bottom-to-top priming operation.

14. A preassembled PBY circuit comprising a blood pump, an oxygenator, a blood line, a filter/trap, a cannulae line subassembly, and a return line serially arranged in a closed loop configuration, and means for attaching a prime line in fluid communication with said circuit, the cannulae line subassembly including a first cannula line attached to the return line, a second cannula line attached to the filter/trap, and means for connecting the first and second cannulae lines in fluid communication, said circuit being arranged for suspension such that, when suspended, the filter/trap is located at a high point of the circuit, and the prime line attaching means is located at a low point of the circuit, such that, when a prime line is attached to the circuit, priming fluid introduced through the prime line enters at a low point of the circuit, and fills the circuit in a bottom-to-top priming operation.

15. A circuit as recited in claim 14, wherein each of said first and second cannulae lines is prearranged in a helical configuration such that, when the circuit is suspended, said cannulae line subassembly provides a continuous vertical rise for priming.

16. A circuit as recited in claim 14, wherein said blood pump is a roller pump including a pump chamber formed by a flexible tube.

17. A circuit as recited in claim 16, wherein the flexible tube pump chamber of said blood pump is arranged in a helical configuration.

18. A circuit as recited in claim 17, wherein said flexible tube pump chamber is arranged in a helical configuration such that, when the circuit is suspended for priming, the helical configuration provides a continuous vertical rise.

19. A circuit as recited in claim 14, wherein said blood pump is a single roller blood pump including a pump chamber formed by a flexible tube, said flexible tube being prearranged in a helical configuration such that, when the circuit is suspended for priming, the flexible tube pump chamber provides a continuous vertical rise.

20. A circuit as recited in claim 14, wherein said blood pump and said oxygenator form an integral unit.

21. A circuit as recited in claim 19, wherein said blood pump and said oxygenator are combined to form an integral unit.

22. A circuit as recited in claim 19, wherein said cannulae line subassembly is prepackaged in tear-apart container means for maintaining said cannulae lines in a predetermined configuration, such that, when the circuit is suspended for priming, said cannulae line subassembly provides a continuous vertical rise for priming.

23. A circuit as recited in claim 15, wherein said cannulae line subassembly is prepackaged in tear-apart container means for maintaining said cannulae lines in a helical configuration, such that, when the circuit is suspended for priming, said cannulae line subassembly provides a continuous vertical rise for priming.

24. A circuit as recited in claim 14, wherein said circuit is prepackaged in container means for maintaining each of said blood pump, oxygenator, blood line, filter/trap, cannulae line subassembly and return line in a configuration having a continuous vertical rise when said circuit is suspended for priming.

25. A circuit as recited in claim 14, wherein said return line comprises said means for attaching a prime line.

26. A preassembled circuit for an extracorporeal bypass procedure, the circuit comprising a blood pump, a blood line, a filter/trap, a cannulae line subassembly, and a return line serially arranged in a closed-loop configuration, and means for attaching a prime line in fluid communication with the circuit, the cannulae line subassembly including a first cannula line attached to the return line, a second cannula line attached to the filter/trap, and means for connecting the first and second cannulae lines in fluid communication, the circuit being arranged for suspension such that, when suspended, the filter/trap is located at a high point of the circuit, and the prime line attaching means is located at a low point of the circuit, such that, when a prime line is attached to the circuit, priming fluid introduced through the prime line enters at a low point of the circuit, and fills the circuit in a bottom-to-top priming operation.

27. A circuit as recited in claim 26, wherein each of said cannulae lines is prearranged in a helical configuration, such that, when the circuit is suspended, said cannulae line subassembly provides a continuous vertical rise for priming.

28. A circuit as recited in claim 26, wherein said blood pump is a roller pump including a pump chamber formed by a flexible tube.

29. A circuit as recited in claim 28, wherein the flexible tube pump chamber of said blood pump is arranged in a helical configuration.

30. A circuit as recited in claim 29, wherein said flexible tube pump chamber is arranged in a helical configuration such that, when the circuit is suspended for priming, the helical configuration provides a continuous vertical rise.

31. A circuit as recited in claim 26, wherein said blood pump is a single roller blood pump including a pump chamber formed by a flexible tube, said flexible tube being prearranged in a helical configuration, such that, when the circuit is suspended for priming, the flexible tube pump chamber provides a continuous vertical rise.

32. A circuit as recited in claim 26, wherein said cannulae line subassembly is prepackaged in tear-apart container means for maintaining said cannulae line assembly in a predetermined configuration, such that, when the circuit is suspended for priming, said cannulae line subassembly provides a continuous vertical rise for priming.

33. A circuit as recited in claim 27, wherein said cannulae line subassembly is prepackaged in tear-apart container means for maintaining said cannulae line assembly in a helical configuration, such that, when the circuit is suspended for priming, said cannulae line subassembly provides a continuous vertical rise for priming.

34. A circuit as recited in claim 26, wherein said circuit is prepackaged in container means for maintaining each of said blood pump, blood line, filter/trap, cannulae line subassembly and return line in a configuration having a continuous vertical rise when said circuit is suspended for priming.

35. A circuit as recited in claim 26, wherein said return line comprises said means for attaching a prime line.

36. A preassembled circuit for an extracorporeal procedure, the circuit comprising a blood pump, an oxygenator, a blood line, a filter/trap, a cannulae line subassembly, and a heat exchanger line subassembly serially arranged in a closed-loop configuration, and means for attaching a prime line in fluid communication with the circuit, the cannulae line subassembly including a first cannula line attached to the return line, a second cannula line attached to the filter/trap, and means for connecting the first and second cannulae lines in fluid communication, the circuit being arranged for suspension such that, when suspended, the filter/trap is located at a high point of the circuit, and the prime line attaching means is located at a low point of the circuit, such that, when a prime line is attached to the circuit, priming fluid introduced through the prime line enters at a low point of the circuit, and fills the circuit in a bottom-to-top priming operation.

37. A circuit as recited in claim 36, wherein each of said cannulae lines is prearranged in a helical configuration, such that, when the circuit is suspended, said cannulae line subassembly provides a continuous vertical rise for priming.

38. A circuit as recited in claim 36, wherein said blood pump is a roller pump including a pump chamber formed by a flexible tube.

39. A circuit as recited in claim 38, wherein the flexible tube pump chamber of said blood pump is arranged in a helical configuration.

40. A circuit as recited in claim 39, wherein said flexible tube pump chamber is arranged in a helical configuration such that, when the circuit is suspended for priming, the helical configuration provides a continuous vertical rise.

41. A circuit as recited in claim 36, wherein said blood pump is a single roller blood pump including a pump chamber formed by a flexible tube, said flexible tube being prearranged in a helical configuration, such that, when the circuit is suspended for priming, the flexible tube pump chamber provides a continuous vertical rise.

42. A circuit as recited in claim 36, wherein said cannulae line subassembly is prepackaged in tear-apart container means for maintaining said cannulae line assembly in a predetermined configuration, such that, when the circuit is suspended for priming, said cannulae line subassembly provides a continuous vertical rise for priming.

43. A circuit as recited in claim 37, wherein said cannulae line subassembly is prepackaged in tear-apart container means for maintaining said cannulae line assembly in a helical configuration, such that, when the circuit is suspended for priming, said cannulae line subassembly provides a continuous vertical rise for priming.

44. A circuit as recited in claim 36, wherein said circuit is prepackaged in container means for maintaining each of said blood pump, blood line, filter/trap, cannulae line subassembly and return line in a configuration having a continuous vertical rise when said circuit is suspended for priming.

45. A circuit as recited in claim 36, wherein said heat exchanger line subassembly includes a heat exchanger reservoir line and a reservoir bypass line, and wherein said reservoir line comprises said means for attaching a prime line.

\* \* \* \* \*